United States Patent [19]

Schaetzle et al.

[11] Patent Number: 5,391,140
[45] Date of Patent: Feb. 21, 1995

[54] THERAPY APPARATUS FOR LOCATING AND TREATING A ZONE IN THE BODY OF A LIFE FORM WITH ACOUSTIC WAVES

[75] Inventors: Ulrich Schaetzle, Roettenbach; Bernd Granz, Oberasbach, both of Germany

[73] Assignee: Siemens Aktiengesellschaft, Munich, Germany

[21] Appl. No.: 172,732

[22] Filed: Dec. 27, 1993

[30] Foreign Application Priority Data

Jan. 29, 1993 [DE] Germany .................. 4302537

[51] Int. Cl.6 .................................. A61B 17/22
[52] U.S. Cl. ............................ 601/4; 128/660.03
[58] Field of Search ............. 601/2.4; 128/660.03

[56] References Cited

U.S. PATENT DOCUMENTS

| | | | |
|---|---|---|---|
| 4,159,462 | 6/1979 | Rocha et al. | 340/1 R |
| 4,526,168 | 7/1985 | Hassler et al. | 601/4 |
| 4,584,880 | 4/1986 | Matzuk | 73/609 |
| 4,915,114 | 4/1990 | Hassler | 128/660.03 |
| 4,955,365 | 9/1990 | Fry et al. | 601/2 |
| 5,143,073 | 9/1992 | Dory | 128/660.03 |
| 5,150,712 | 9/1992 | Dory | 128/660.03 |
| 5,174,294 | 12/1992 | Saito et al. | 601/4 |
| 5,176,142 | 1/1993 | Mason | 128/662.06 |
| 5,215,091 | 6/1993 | Ishida | 601/4 |
| 5,241,962 | 9/1993 | Iwama | 601/4 |
| 5,243,985 | 9/1993 | Aida et al. | 601/4 |

FOREIGN PATENT DOCUMENTS 4205030  9/1992  Germany .

OTHER PUBLICATIONS

"Ultrasound Intacavity System for Imaging, Therapy Planning and Treatment of Focal Disease" Sanghvi et al, Preprint from 1992 IEEE Ultrasonics, Ferroelectrics, and Frequency Control Syposium.

Primary Examiner—Lee S. Cohen
Assistant Examiner—Brian L. Casler
Attorney, Agent, or Firm—Hill, Steadman & Simpson

[57] ABSTRACT

A therapy apparatus for locating and treating a zone in the body of a living subject with focused, therapeutic ultrasound waves having a first frequency includes an ultrasound locating system which emits diagnostic ultrasound having a second frequency, and which receives parts of the diagnostic ultrasound reflected in the body of the subject and converts them into electrical signals which are used to form an image of the zone to be treated with the subject. In order to permit the locating system to be operated simultaneously with the generation of therapeutic waves, and thus to be able to generate a continuous image without disturbances caused by therapeutic waves, the electrical signals are supplied, before forming the image, to a filter having a transfer function with a rejection band wherein the first frequency lies and a passband wherein the second frequency lies. The output signals from the filter are then used to generate the image.

29 Claims, 6 Drawing Sheets

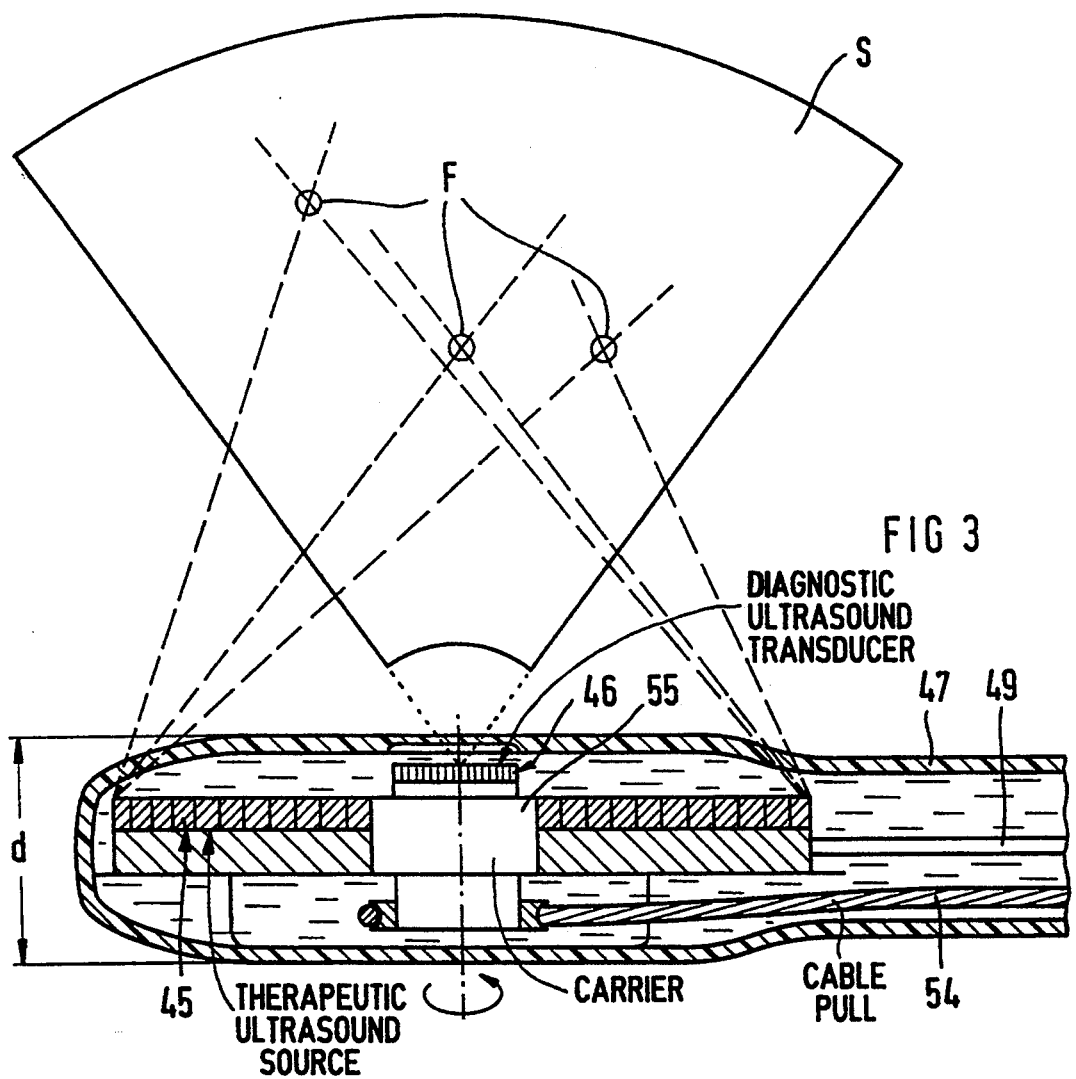
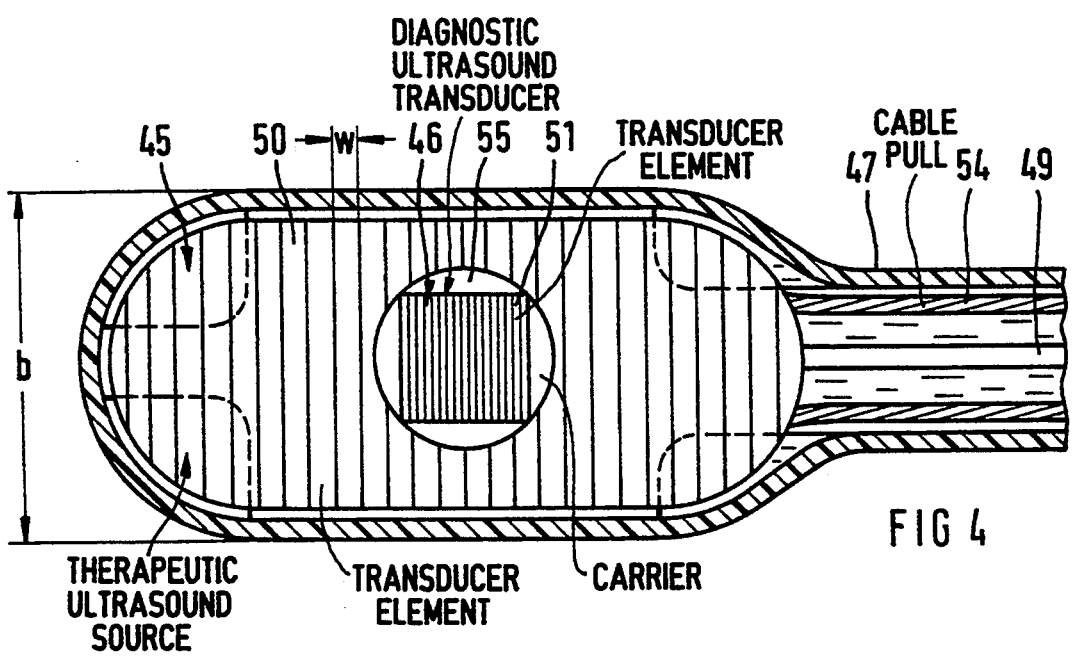

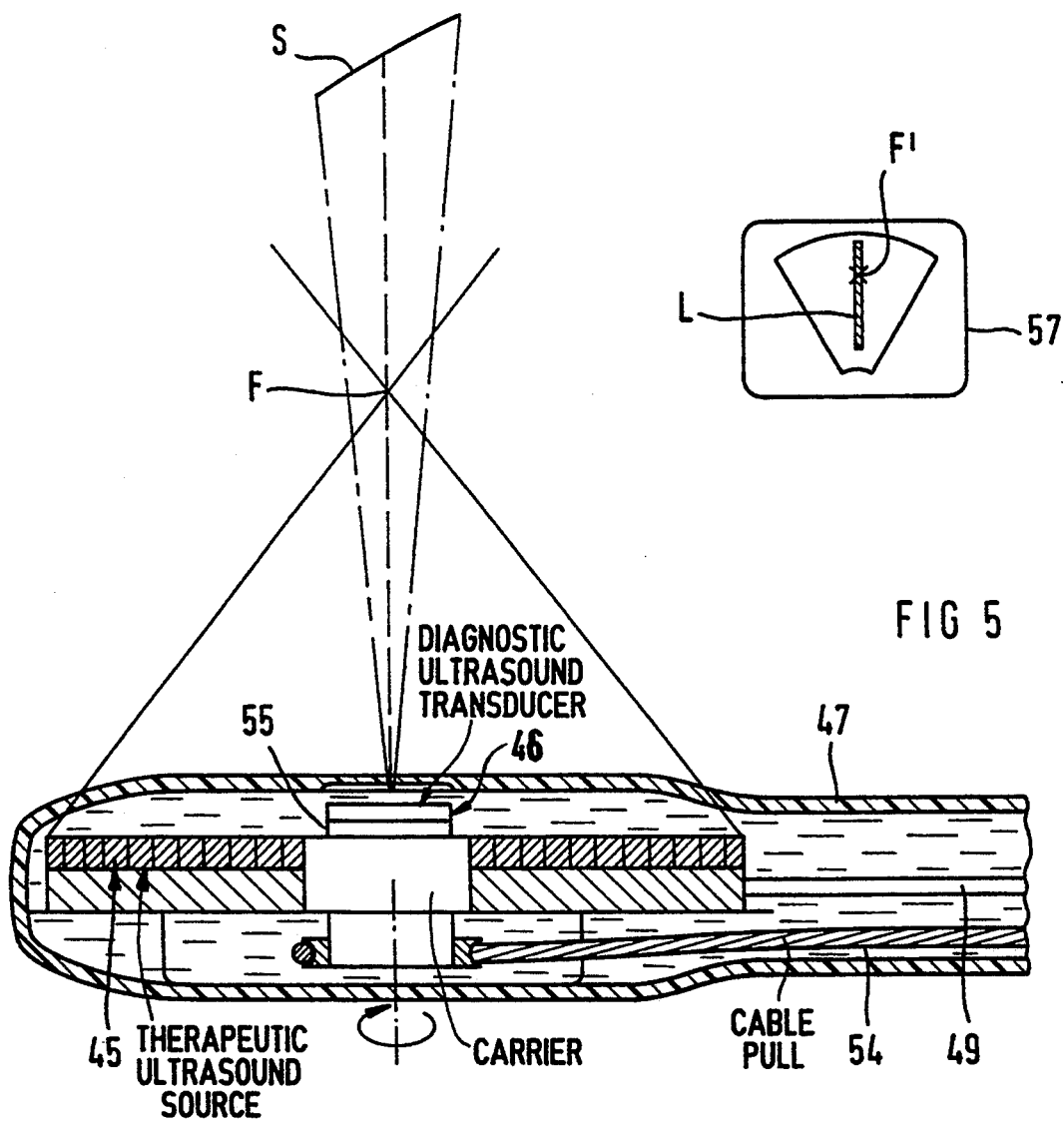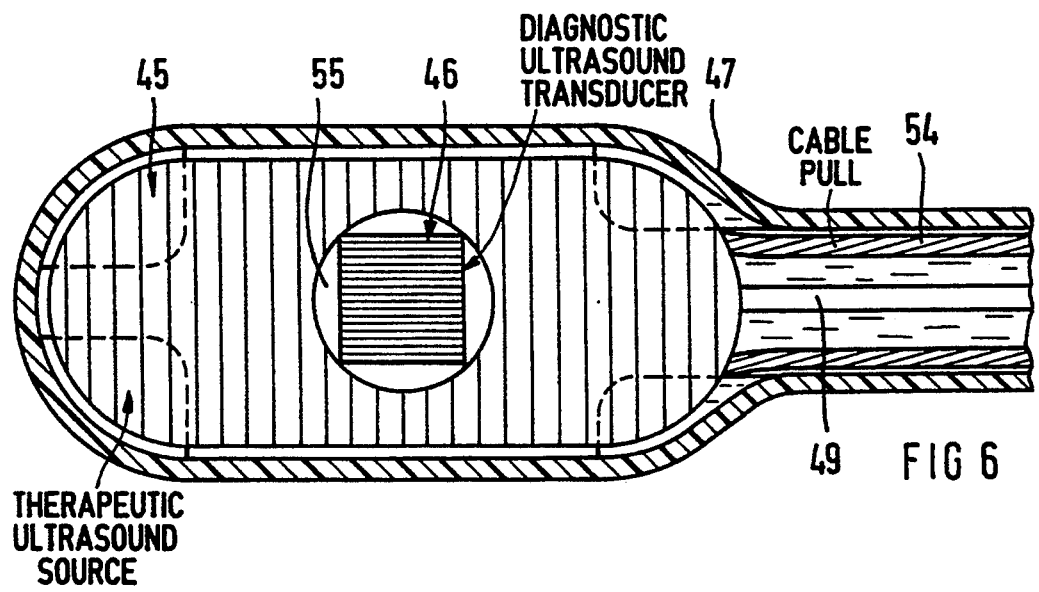

THERAPY APPARATUS FOR LOCATING AND TREATING A ZONE IN THE BODY OF A LIFE FORM WITH ACOUSTIC WAVES

BACKGROUND OF THE INVENTION

1. Field of the Invention

The present invention is directed to a therapy apparatus for locating and treating a zone in the body of a living subject with acoustic waves, of the type having a source of acoustic waves which generates therapeutic acoustic waves having a first frequency that are focused onto a zone of action and an acoustic locating means which transmits diagnostic acoustic waves having a second frequency, and which receives parts of the diagnostic acoustic waves reflected in the body of subject and, converts them into electrical signals which are used as image information with respect to the zone to be treated.

2. Description Of the Prior Art

Therapy systems which emit focused ultrasound waves as therapeutic acoustic waves and diagnostic ultrasound as diagnostic acoustic waves are employed, for example, for the treatment of pathological tissue (see, for example, European Application 0 339 639, corresponding to U.S. Pat. Nos. 5,150,712 and 5,143,073, and Ultrasound Intracavity System for Imaging, Therapy Planning and Treatment of Focal Disease", Sanghvi et al., Reprint from 1992, IEEE Ultrasonic, Ferroelectrics and Frequency Control Symposium). The pathological tissue is heated by the focused ultrasound waves. If the resulting temperatures lie below 45° C., the cell metabolism is disturbed, resulting in a retardation of the growth, or a shrinking of, treated tissue mass, such as a tumor. This type of treatment is known as local hyperthermia. When temperatures beyond 45° C. are achieved, the cell protein coagulates, with the result that the tissue is necrotized. This latter type of treatment is referred to as thermotherapy.

Different frequencies for the therapeutic and for the diagnostic ultrasound waves are employed in order to enable an optimum matching to the respective task, therapy or diagnostics. As a rule, the frequency of the therapeutic ultrasound waves will be selected relatively low for achieving low attenuation, whereas that of the diagnostic ultrasound waves will be selected relatively high in order to achieve a good topical resolution.

In known therapy systems of the type initially cited, the therapeutic ultrasound source and the ultrasound locating means can generally not be simultaneously operated, since the operation of the therapeutic ultrasound source leads to image disturbances in the image produced by the ultrasound locating means, so that a proper locating of the zone to be treated is not possible. Except in unusual cases wherein echo signals of the therapeutic acoustic waves are to be evaluated, for example as described in German OS 42 05 030, one usually proceeds as described in European Application 0 339 693 such that the therapeutic ultrasound source and the ultrasound locating means are operated in alternation, namely such that relatively long treatment intervals and relatively short locating intervals follow one another in alternation. This means that a continuous locating of the zone to be treated is not possible.

U.S. Pat. No. 4,584,880 discloses an ultrasound imaging apparatus wherein a filter having a bandpass-like filter characteristic is provided at the reception side. This filter is provided in order to be able to image regions lying deeply within the subject to be imaged with improved image quality. Since, in comparison to the emitted ultrasound pulses, the frequency spectrum of the received echo signals becomes lower in frequency as the depth from which the echo signals derive increases, the passband of the filter is shifted toward lower frequencies following each transmission of an ultrasound pulse (and the gain is increased at the same time). A continuous locating and monitoring of the zone to be treated would not be enabled, however, by applying these known measures in a therapy apparatus of the type initially cited.

SUMMARY OF THE INVENTION

It is an object of the present invention to provide a therapy apparatus of the type initially cited wherein a continuous locating and monitoring of the zone to be treated is possible.

This object is achieved in accordance with the principles of the present invention in a therapy apparatus and method for locating and treating a zone in the body of a living subject with acoustic waves, having the following features.

A source of acoustic waves which generates therapeutic acoustic waves of a first frequency focused onto a zone of action. An acoustic locating means is operated simultaneously with the source, said acoustic locating means transmitting diagnostic acoustic waves of a second frequency, and receiving parts of the diagnostic acoustic waves reflected in the body of the subject and, converting them into electrical signals for use as image information with respect to the zone to be treated. The locating means is made operable simultaneously with the source of therapeutic acoustic waves by providing the locating means with a filter for suppressing at least the fundamental wave of the focused, therapeutic acoustic waves, the transfer function of this filter having a non-passing (blocking) band wherein the first frequency lies and having a passband wherein the second frequency lies.

The invention thus makes use of the fact that the source of acoustic waves and the locating means transmit acoustic waves having different frequencies and, on the basis of a filter having a suitable transfer function, blanks those signal parts of the electrical signals that do not correspond to portions of the diagnostic acoustic waves reflected in the body of the subject, but instead correspond to the therapeutic acoustic waves. The source of therapeutic acoustic waves and the locating means can thus be simultaneously operated without noteworthy disturbances of the image produced by the locating means occurring due to the therapeutic acoustic waves. The image data supplied by the locating means with respect to the zone to be treated preferably refers to the position of the zone of action of the therapeutic acoustic waves relative to the zone to be treated. The image data are preferably real-time data.

Although it is possible also to employ a part of the source of acoustic waves (the therapeutic ultrasound source) for emitting the diagnostic ultrasound (in which case, the source of acoustic waves or the therapeutic ultrasound source would then be a component of the ultrasound locating means), in an embodiment of the invention the ultrasound locating means contains at least one diagnostic ultrasound transducer which is exclusively used to generate the diagnostic ultrasound and to receive parts of the diagnostic ultrasound reflected in the body and to convert them into electrical signals.

In a further embodiment of the invention the ultrasound locating means includes an image-generating electronics for generating ultrasound images to which the electrical signals are supplied, and which contains the aforementioned filter.

In a preferred embodiment of the invention, the ultrasound locating means offers image data in the form of real-time ultrasound images, preferably ultrasound B-images. Such ultrasound images allow an extremely exact monitoring of the zone to be treated, particularly of the position thereof relative to the zone of action.

For the reasons already set forth, in a version of the invention the first frequency is lower than the second.

It is adequate in many instances for the filter to be a high-pass filter. The limit frequency thereof essentially coincides with the second frequency, or lies slightly below it. It is assured in this way that the influences of the therapeutic acoustic waves are extremely slight since, given an adequate edge steepness of the filter and a first frequency lying adequately far below the limit frequency of the filter (the limit frequency corresponding to the fundamental of the therapeutic acoustic waves) only reflected parts of harmonics of the therapeutic acoustic waves are contained in the output signal of the filter. According to further versions of the invention, however, the filter can be a band rejection filter or bandpass filter. If a band rejection filter is used, the center frequency of the band rejection filter coincides with the first frequency. If a bandpass filter is used, the center frequency of the bandpass filter coincides with the second frequency. The employment of a band rejection filter can be particularly expedient when the second frequency, in a further version of the invention, is adjustable for matching the operating parameters of the locating means to the particular treatment case.

When the therapy apparatus is provided for rectal application, for example for treating benign prostate hyperplasia, it is expedient to fashion at least one of the therapeutic ultrasound source or the diagnostic ultrasound transducer as a phased array. In this case, it is possible to displace the zone of action, or to scan the subject to be treated with the diagnostic ultrasound waves, in the way required for producing ultrasound B-images as disclosed by U.S. Pat. No. 4,526,168 without the need for mechanisms to physically displace the transducers, thereby saving space. The phased array is preferably fashioned as a linear array, since it is then possible to displace the zone of action in a plane, or to displace the center axis of the diagnostic ultrasound in the fashion of a linear scan or sector scan. In order to achieve a mechanical pre-focusing of the therapeutic ultrasound waves, or of the diagnostic ultrasound, in a further version the linear array is curved around its longitudinal axis as described in U.S. Pat. No. 4,159,462 in conjunction with diagnostic ultrasound transducers.

In order to be able to produce ultrasound images of multiple body slices of the subject to be treated, respectively having different positions with regard to the source of acoustic waves, provided in a preferred embodiment of the invention the diagnostic ultrasound transducer can be turned relative to the source of acoustic waves. A diagnostic ultrasound transducer capable of being turned is disclosed by U.S. No. 5,176,142.

DESCRIPTION OF THE DRAWINGS

FIGS. 3 through 7 respectively show a therapy apparatus of the invention provided for rectal application shown in various sections and operating modes.

DESCRIPTION OF THE PREFERRED EMBODIMENTS

Figure 1:
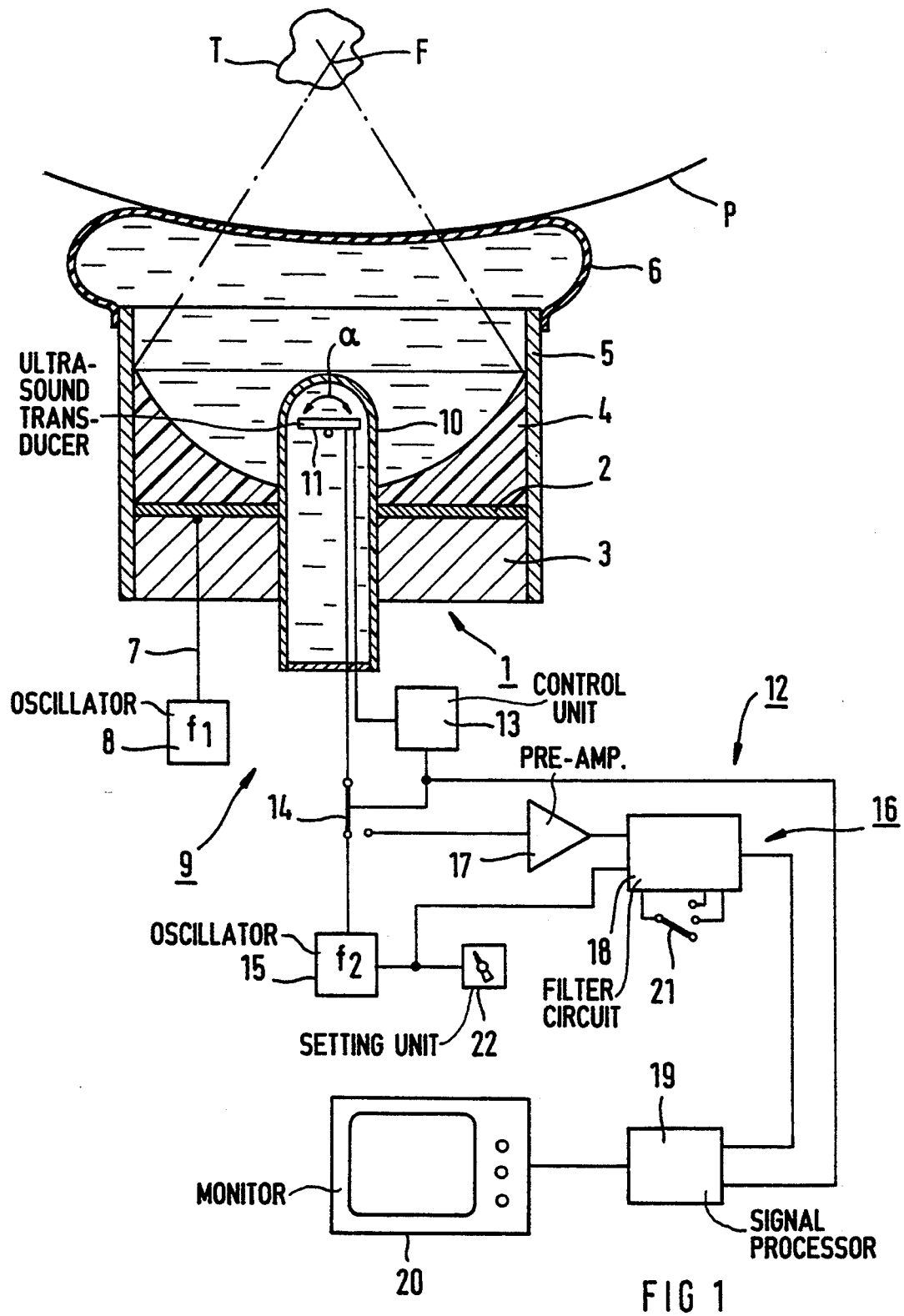
FIG. 1 is a schematic illustration of a therapy apparatus constructed and operating in accordance with the principles of the present invention.

The therapy apparatus shown in FIG. 1 contains a therapeutic ultrasound source that generally is referenced 1, as a source of acoustic waves. The source 1 contains a planar, piezoelectric ultrasound transducer 2 that is applied to one end face of an acoustically hard or acoustically soft carrier member 3. A planoconcave acoustic positive lens 4 is connected to an end face of the ultrasound transducer 2 facing away from the carrier member 3, the positive lens 4 focusing the ultrasound waves emanating from the ultrasound transducer 2 onto a zone of action whose center is referenced F in FIG. 1. The ultrasound source 1 is accepted in a housing 5 filled with a liquid acoustic propagation medium, for example water, the application end thereof being closed with a resilient coupling cushion 6. The coupling cushion 6 serves the purpose of acoustic coupling to the body surface of a living subject to be treated, for example a patient P, and is pressed against the body surface thereof.

The ultrasound transducer 2, which can be a one-piece piezoceramic part or can be composed of a mosaic arrangement of a plurality of small piezoceramic elements, has end faces provided with electrodes in a known manner and, as schematically indicated in FIG. 1, is in communication via a line 7 with an electrical oscillator 8. The oscillator drives the ultrasound source 1 to generate focused, therapeutic acoustic waves, specifically focused therapeutic ultrasound waves having a first frequency f1. The thickness of the ultrasound transducer 2 and of the carrier member 3 are dimensioned in accord so as to achieve the first frequency f1 in a known way.

The therapy apparatus of FIG. 1 also has an acoustic locating means generally referenced 9 which contains an ultrasound head 10 that, for example, is a mechanical sector scanner. This is illustrated in FIG. 1 in that an ultrasound transducer referenced 11 is shown which executes an oscillatory pivoting motion in the direction of the double arrow $\alpha$ around an axis proceeding at a right angle relative to the plane of the drawing. The ultrasound head 10 is accepted liquid-tight in a central bore of the ultrasound source 1 and can be adjustable (in a known manner not shown) relative to the ultrasound source 1 in order to be able to select a beneficial alignment relative to the patient P for a particular treatment.

The ultrasound transducer 11 of the ultrasound head 10 is in communication with image-generating electronics 12 via a schematically indicated line. The image-generating electronics 12 is fashioned in a known way, except for one difference as set forth below. Consequently, the electronics 12 include a control unit 13 that, first, controls the mechanical swivel motion of the ultrasound transducer 11 and, second, controls the position of a switch 14. Dependent on the switch position, the ultrasound transducer 11 is connected via the switch 14 either to an electrical oscillator 15 or to an image formatting circuit generally referenced 16. The control by means of the control unit 13 ensues such that the ultrasound transducer 11 is first connected with the switch 14 to the oscillator 15 during a swivel motion of the ultrasound transducer from one extreme position to another extreme position for a defined plurality of angular positions, for example 256 angular positions of the ultrasound transducer 11, and is driven by the oscillator 15 to emit diagnostic acoustic waves, namely a known, pulse-like diagnostic ultrasound signal. The control unit 13 subsequently causes the transducer 11 to be connected via the switch 14 to the image formatting circuit 16. The image formatting or image-generating electronics circuit/16 is supplied with electrical signals converted from the parts of the diagnostic ultrasound reflected in the body of the patient P and which are received with the ultrasound transducer 11. The frequency of the oscillator 15 is selected such that the diagnostic ultrasound has a second frequency f2 that is different from the first frequency f1, and preferably exceeds the first frequency f1.

In the image formatting circuit 16, the electrical signals of the ultrasound transducer 11 first proceed to a pre-amplifier 17. The output thereof is connected to the input of a filter circuit 18 whose output is in turn connected to the input of a signal processor 19 that, as an output signal, supplies a video signal corresponding to the generated ultrasound image which is displayed on a monitor 20. *

*The difference mentioned above except from which the image formatting circuit 16 is conventional is the presence of filter circuit 18.

The filter circuit 18 has a transfer function resulting in that an amplitude frequency response having a nonpass band wherein the first frequency f1 lies. The amplitude frequency response is also selected such that signals of the second frequency f2 can pass the filter circuit 18 substantially unattenuated.

Thus parts of the therapeutic ultrasound waves received with the ultrasound transducer 11 (which can be reflected parts or parts emitted directly by the therapeutic ultrasound source 1) do not result in any image disturbances of the ultrasound locating means 9 since the corresponding parts of the electrical signals of the ultrasound transducer 11 are filtered out by the filter circuit 18. The therapeutic ultrasound source 1 and the ultrasound locating means 9 can thus be unproblematically operated at the same time, so that a continuous monitoring and locating of the zone to be treated, for example a tumor T, is guaranteed.

The type of transfer function of the filter circuit 18 can be switched, this being schematically indicated by a switch 21 connected to the filter circuit 18. In a first position of the switch 21, the filter circuit 18 has the transfer function of a high-pass filter. In order to achieve a maximum filter effect for a given order of the transfer behavior of the filter circuit 18, it is then expedient to select the transfer frequency of the transfer function such that its is at most equal to the second frequency f2.

In a second position of the switch 21, the filter 18 has the transfer function of a band rejection filter. In this case, the center frequency of the transfer function, i.e. that frequency at which the greatest attenuation of the output signal of the filter circuit 18 occurs, corresponds to the frequency of the therapeutic ultrasound waves, i.e. to the first frequency f1.

In a third position of the switch 21, the filter circuit 18 has the transfer function of a bandpass filter. In this case, the center frequency of the transfer function corresponds to the frequency of the diagnostic ultrasound, i.e. to the second frequency f2.

In order to be able to adapt the frequency of the diagnostic ultrasound to the requirements of the respective therapy case individually in view of the required penetration depth, or in view of the desired topical resolution, it is provided that the second frequency f2 is variable. This is schematically indicated in FIG. 1 by a setting unit 22. The setting unit 22 acts not only on the oscillator 15 but also on the filter circuit 18, and matches the transfer function of the filter circuit 18 to the second frequency f2 that is respectively set, insofar as high-pass or bandpass behavior is selected as the transfer function with the switch 21.

Instead of focusing the therapeutic ultrasound waves with a positive lens 4, moreover, the ultrasound transducer 2 can be provided in a known manner with an emission surface that is curved, preferably spherically curved, such that the generated therapeutic ultrasound waves are concentrated onto a focus zone.

Figure 2:
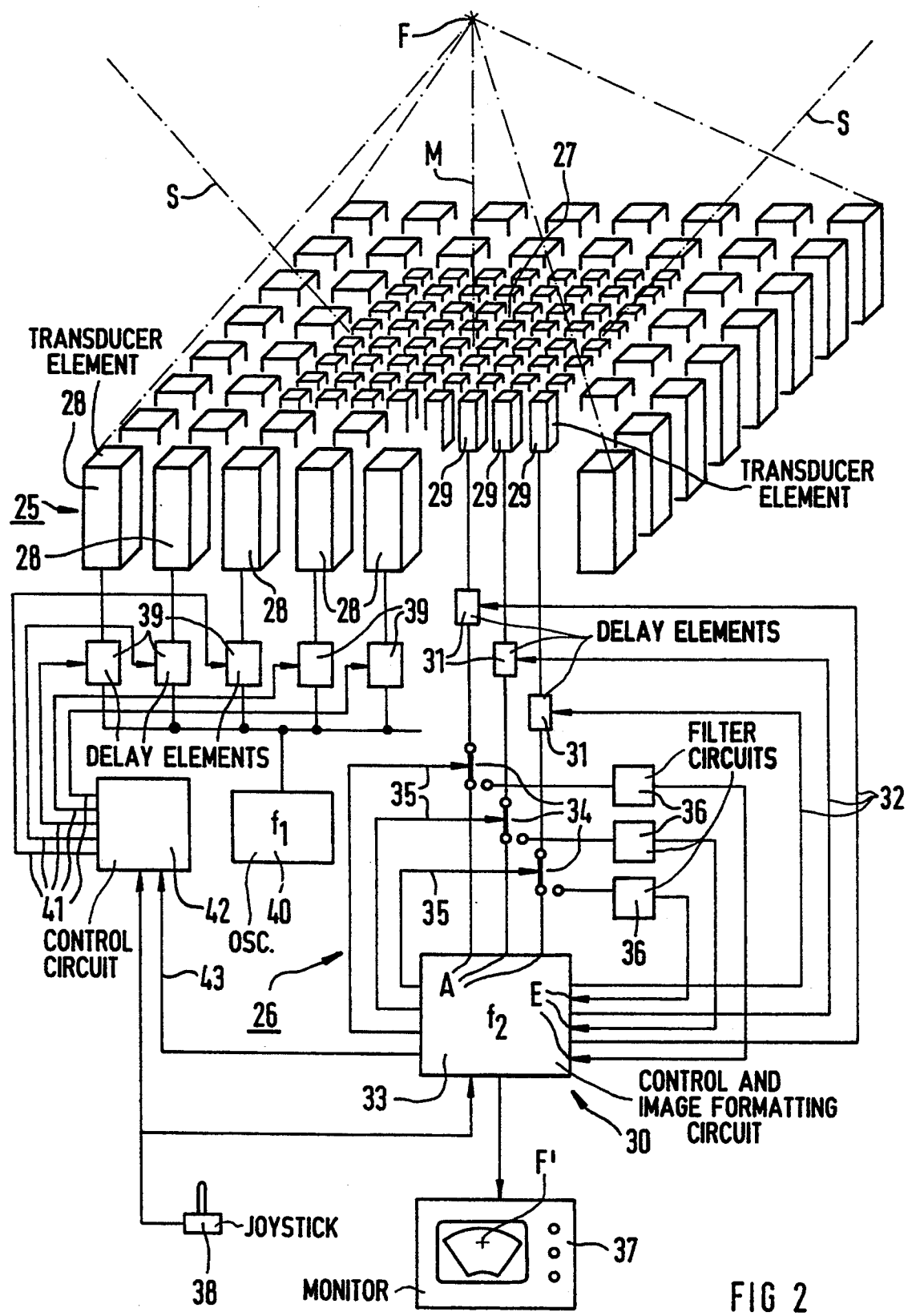
FIG. 2 is a schematic, partially perspective illustration of a further embodiment of the therapy apparatus of the invention.
Figure 7:
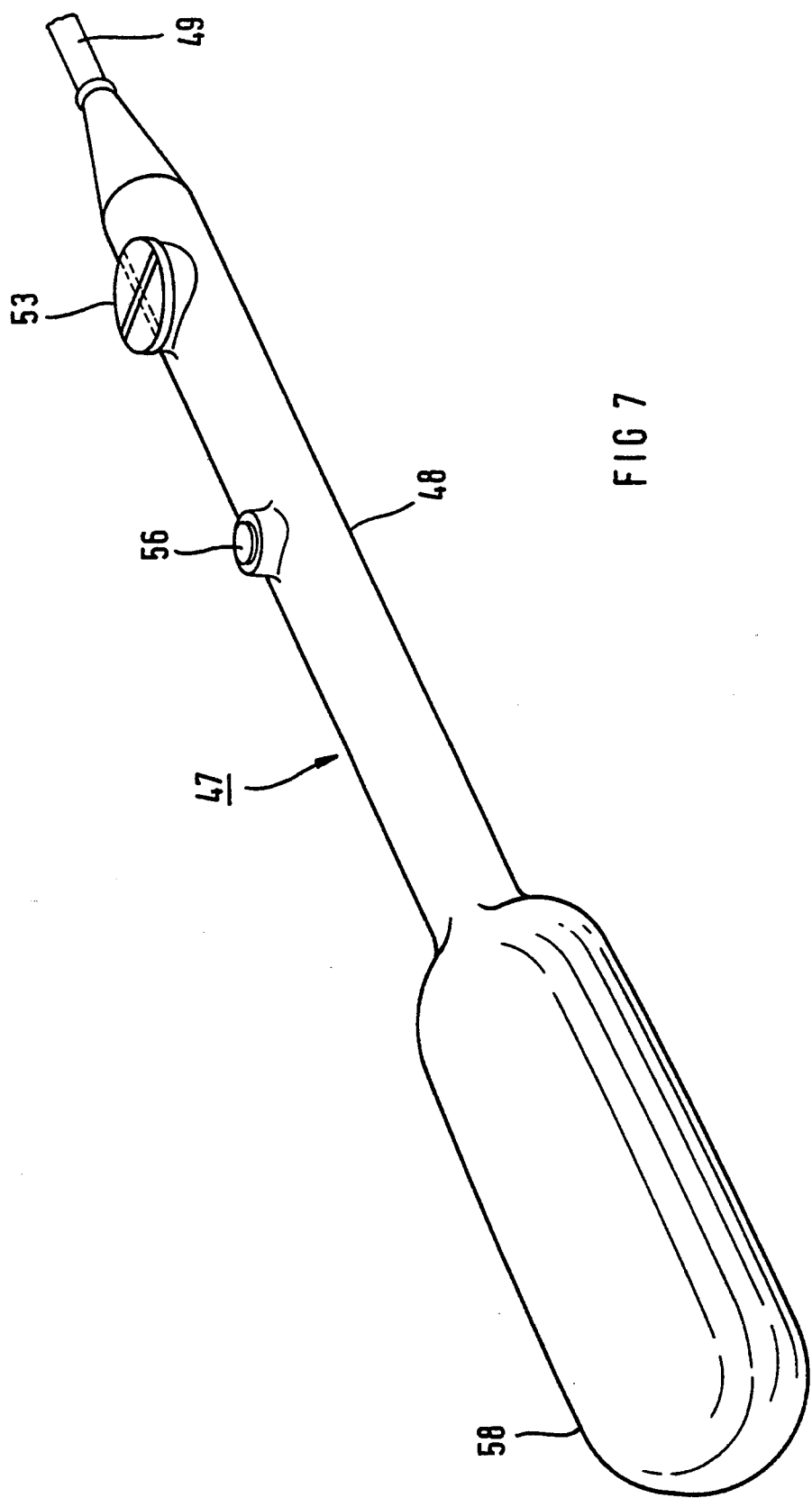

The therapy apparatus schematically shown in FIG. 2 differs from that set forth above in that the focusing of the therapeutic ultrasound waves as well as the scanning of the body of the patient with diagnostic ultrasound required for producing an ultrasound image ensue electronically as disclosed, for example, in German OS 31 19 295, which corresponds to the aforementioned U.S. Pat. No. 4,526,168.

To this end, both the ultrasound source 25 serving the purpose of generating the therapeutic ultrasound waves, as well as the ultrasound transducer 27 belonging to the ultrasound locating system 26, are each composed of a matrix of a plurality of piezoelectric ultrasound transducer elements 28 or 29, whereby only a few ultrasound transducer elements respectively carry the corresponding reference numerals in FIG. 2 for clarity.

The ultrasound transducer elements 29 of the ultrasound transducer 27 are in communication with the image-generating electronics 30 of the ultrasound locating system 26, as is shown by an example in FIG. 2 for three ultrasound transducer elements 29. The image-generating electronics 30 contains a delay element 31 for each of the ultrasound transducer elements 29, the respective delay times thereof being individually adjustable by a control and image formatting circuit 33 via a line 32. The respective delay elements 31 each have their other terminal connected to a switch 34 via which they are optionally connected to an output A allocated to the respective ultrasound transducer element 29, or to an input E of the control and image formatting circuit 33. The switches 34 are actuated by the control and image formatting circuit 33 via lines 35. When the switches 34 respectively assume their positions shown in FIG. 2, the ultrasound transducer elements 29 are connected via the outputs A to an electrical oscillator contained in the control and image formatting circuit 33, this electrical oscillator driving them pulse-like to generate diagnostic ultrasound having the second frequency f2. The electrical signals generated by the ultrasound transducer elements 29 following their drive, due to the reception of reflected parts of the diagnostic ultrasound are supplied to the input E of the control and image formatting circuit 33 by switching the switches 34 into their other position (not shown). In this other position, the output signals of the ultrasound transducer elements 29 proceed via respective filter circuits 36 to the corresponding input of the control and image formatting circuit 33. The latter sets the delay times of the delay elements 31 such that a scanning of the body of the patient with diagnostic ultrasound ensues in the desired way. As indicated in FIG. 2, the canning scan ensue, for example, in the form of a sector scan - the corresponding sector S is indicated in FIG. 2 - or can ensue in the form of a parallel scan, whereby the scanned body slice can assume nearly arbitrary angular positions with respect to the center axis M of the arrangement of the ultrasound transducer elements 28 and 29 (within the limits of the adjustability of the delay times of the delay elements 31).

The ultrasound image obtained in this manner is displayed on a monitor 37 connected to the control and image formatting circuit 33.

A delay element is also allocated to each of the ultrasound transducer elements 28 of the therapeutic ultrasound source 25. These delay elements bear reference numeral 39. The ultrasound transducer elements 28 are connected via the delay elements 39 to an electrical oscillator 40 that drives the ultrasound transducer elements 28, and thus the therapeutic ultrasound source 25, to emit therapeutic ultrasound waves having the first frequency f1. The delay times of the delay elements 39 are set such via lines 41 by a control circuit 42 such that the therapeutic ultrasound waves are focused onto a zone of action. The control circuit 42 first sets the delay times such that the zone of action lies within the body slice of the patient scanned with the diagnostic ultrasound. Data about the respective position of the slice scanned with the diagnostic ultrasound are supplied to the control circuit 42 by the control and image formatting circuit 33 via a line 43. Second, the control circuit 42 sets the delay times such that the zone of action assumes a position in the slice scanned with the diagnostic ultrasound that was set with a joystick 38. The joystick 38 is connected to the control unit 42 and to the control and image formatting circuit 33; the latter mixes a mark F, corresponding to the position of the joystick 38 into the ultrasound image displayed on the monitor 37. It is thus possible to set the center (referenced F in FIG. 2) of the zone of action of the therapeutic ultrasound waves to the desired point of the displayed ultrasound image with the joystick 38 and with the mark F, mixed into the ultrasound image.

The filter circuits 36 each have the same transfer function that includes a non-pass band wherein the first frequency f1 lies and comprises a passband wherein the second frequency f2 lies. It is thus also assured in the case of the therapy apparatus of FIG. 2 that the focused ultrasound waves emanating from the therapeutic ultrasound source 1 do not cause image disturbances of the ultrasound locating means 26 given simultaneous operation of the therapeutic ultrasound source 25 and of the ultrasound locating means 26.

A further therapy apparatus of the invention is shown in FIGS. 3 through 7. This is an apparatus for treatment of benign prostate hyperplasia. The therapeutic ultrasound source 45 and the diagnostic ultrasound transducer of the ultrasound locating system are accepted in a handpiece 47 having an approximately spoon shape that is filled with an acoustic propagation medium, for example water. At its thickened end, the handpiece 47 comprises a width b of approximately 30 mm and a thickness d of approximately 15 mm. The approximately cylindrical handle 48 has a diameter of approximately 12 mm. The handpiece 47 can thus be introduced into the rectum of a male patient, whereby the thickened end part 58 containing the therapeutic ultrasound source 45 and the diagnostic ultrasound transducer 46 is completely accepted in the rectum. The handpiece 47 is in communication with the electrical components of the therapy apparatus via a connecting line 49.

The therapeutic ultrasound source 45 and the ultrasound locating transducer 46 are respectively implemented as a linear arrangement of line-shaped ultrasound transducer elements (referred to as a linear array).

The drive of the ultrasound transducer elements 51 of the ultrasound locating transducer 46 ensues in a way analogous to FIG. 2, whereby only one body slice, whose middle plane corresponds to the plane of the drawing with reference to the illustration of FIG. 2, can be scanned as a consequence of the linear arrangement of the ultrasound transducer elements 51. The sector S that can be scanned with the ultrasound locating transducer 46 when the ultrasound transducer elements 51 thereof are driven time-delayed in the way required for the implementation of a sector scan is shown in FIG. 2. The ultrasound transducer elements 51 of the ultrasound locating transducer 46 are driven time-delayed, or phase-delayed, in the fashion of what is referred to as a phased array.

The ultrasound source 45 also operates in the fashion of a phased array, whereby the drive of the ultrasound transducer elements 50 thereof ensues analogously to the drive of the ultrasound transducer elements 28 in the case of FIG. 2. Since, by contrast to FIG. 2, the ultrasound source 45 does not have a matrix-like format but only a linear arrangement, a focusing of the therapeutic ultrasound waves can in fact be effected by a suitable selection of the drive times of the ultrasound transducer elements 50, but the center F of the zone of action can only be displaced in the plane of the drawing with reference to the illustration of FIG. 3. Three possible positions of the center F of the zone of action are shown in FIG. 3 as examples.

If the limitations that arise because only a linear arrangement of the respective ultrasound transducer elements 50 and 51 of the ultrasound source 45 and the ultrasound locating transducer 46 is provided in the case of the therapy apparatus of FIGS. 3 through 7, instead of a matrix-like arrangement, are left out of consideration, the operating mode illustrated in FIGS. 3 and 4 fully coincides with the functioning of the therapy apparatus of FIG. 2. Consequently, the therapy apparatus of FIGS. 3 through 7 includes image generating electronics and a drive for the ultrasound source 45 that is fashioned analogously to FIG. 2 (see components 30 through 42).

Figure 8:
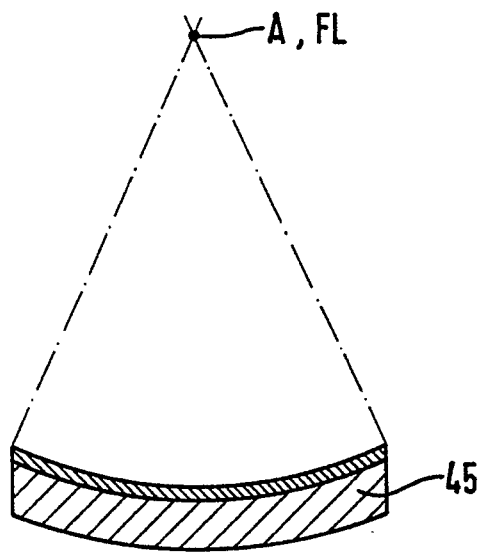
FIGS. 8 and 9 show respective versions of the therapeutic ultrasound source contained in the therapy apparatus according to FIGS. 3 through 6, in cross section.
Figure 9:
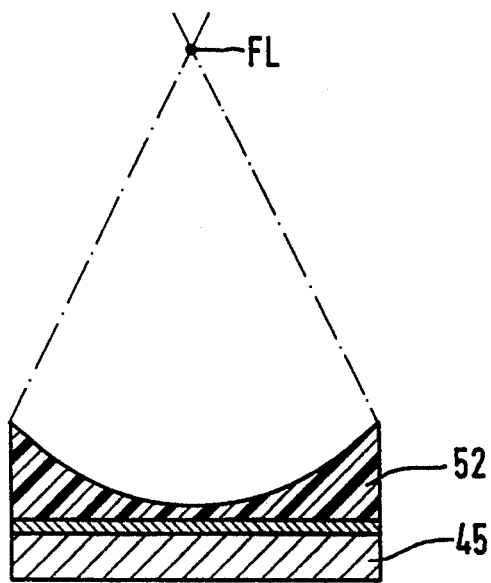

By comparison to a planar embodiment, moreover, the focusing of the ultrasound source 45 can be improved as shown in FIG. 8 by cylindrically curving the ultrasound source 45 around an axis A proceeding parallel to its longitudinal axis. Alternatively, an ultrasound source 45 can be employed that, according to FIG. 9, is preceded by a planoconcave acoustic positive lens 52. In both instances, focusing ensues onto a focal line FL that proceeds parallel to the longitudinal axis of the ultrasound source 45 and that proceeds at a right angle relative to the plane of the drawing in FIGS. 8 and 9.

As may be seen from FIGS. 5 and 6, the ultrasound locating transducer 46 can be turned by 90° by actuating a rotary knob 53 (FIG. 7) so that its longitudinal axis no longer proceeds parallel (as shown in FIGS. 3 and 4) to the longitudinal axis of the ultrasound source 45, but instead proceeds at a right angle thereto. This ensues via a cable pull 54 connected to the rotary knob 53, this cable pull turning a carrier member 55 rotatably seated in the ultrasound source 45. The slice that can be scanned with the ultrasound locating means then no longer proceeds in the plane of the drawing, but instead in a plane residing at a right angle relative to the plane of the drawing as not quite exactly indicated in the perspective view in FIG. 4.

A signal indicating the position of the rotary knob 53 is supplied to the circuits corresponding to the control and image formatting circuit 33 and the control circuit 42 in the case of the therapy apparatus of FIGS. 3 through 7. When this signal indicates that the ultrasound locating transducer 46 has assumed its position shown in FIGS. 5 and 6, a line L is mixed into the ultrasound image 56 as shown in FIG. 5. The line L corresponds to that line in which the center plane of the body slice scanned with the diagnostic ultrasound intersects that plane wherein the center of the focus zone of the diagnostic ultrasound waves can be displaced. The motion of the mark F, is then limited to motions along the line L and the displacement of the center of the zone of action of the therapeutic ultrasound waves is also limited to a corresponding displacement along this straight line.

Thus longitudinal planes (FIGS. 3 and 4) or transversal planes (FIGS. 5 and 6) can be optionally displayed with the ultrasound locating system, and the center F of the zone of action of the therapeutic ultrasound waves in the former instance can be set to arbitrary points within the illustrated transversal slice, whereas the displacement of the center F of the zone of action in the former instance can ensue only along a straight line contained in the longitudinal slice. The employment of the therapy apparatus of FIGS. 3 through 7 ensues by first introducing the handpiece 47 into the rectum of the patient to be treated. Without an emission of therapeutic ultrasound waves, the handpiece 47 is then aligned such that the prostate appears in the ultrasound image. The mark F' identifying the position of the center F of the zone of action of the therapeutic ultrasound waves is then set in the ultrasound image to the desired region of the prostate. A button 56, that corresponds to the switch 43 in the case of FIG. 2 and is provided in the region of the handle 48 is then actuated, the actuation thereof causing the emission of therapeutic ultrasound waves that are focused onto the point marked with the joystick, in addition to the diagnostic ultrasound.

A frequency on the order of magnitude of 2 MHz is suitable as the first frequency f1, i.e. as the frequency for the therapeutic ultrasound waves. A frequency on the order of magnitude of 7 MHz is suitable as the second frequency f2, i.e. as the frequency of the diagnostic ultrasound. When the capability of adjusting the second frequency f2 is provided, a shift of, for example, +3.5 MHz up or down is suitable.

The ultrasound transducer elements 28 and 29 and 50 and 51 are dimensioned in order to avoid a directed emission of the therapeutic ultrasound waves or of the diagnostic ultrasound, so that the smallest expanse of the respective ultrasound transducer element viewed in the emission direction is smaller than half a wavelength of the emitted therapeutic ultrasound waves or of the emitted diagnostic ultrasound. The wavelength in the acoustic propagation medium is thereby the determining factor.

In the case of the therapeutic ultrasound source 45 of the therapy apparatus according to FIGS. 3 through 7, this means that - when the handpiece 47 is filled with water as the acoustic propagation medium and for a frequency of the therapeutic ultrasound waves of 2 MHz - the width of the ultrasound transducer elements 50 referenced w in FIG. 4 cannot be any larger than 0.375 mm, since the sound propagation speed in water lies on the order of magnitude of 1,500 m/s.

An exemplary embodiment of the therapy apparatus that serves the purpose of treating benign prostate hyperplasia was set forth above. However, other therapy system, for example those that serve the purpose of treating tumors or other pathological tissue changes, can also be inventively fashioned.

As used herein, a phased array means an arrangement of a plurality of ultrasound transducer elements that can be electronically focused by chronologically delayed drive signals. A linear array means a linear arrangement of a plurality of ultrasound transducer elements. A scan means, for example, linear or sector-shaped scanning with an ultrasound beam.

Although modifications and changes may be suggested by those skilled in the art, it is the intention of the inventors to embody within the patent warranted hereon all changes and modifications as reasonably and properly come within the scope of their contribution to the art.

We claim as our invention:

1. A therapy apparatus for locating and treating a zone in the body of a living subject with acoustic waves comprising:

means for generating therapeutic acoustic waves at a first frequency and for focusing said therapeutic acoustic waves onto a zone of action; and acoustic locating means for generating an image of a zone to be treated in said subject simultaneously with the generation of therapeutic acoustic waves, for assisting in bringing said zone of action into coincidence with said zone to be treated, said acoustic locating means including means for emitting diagnostic acoustic waves at a second frequency and for receiving parts of said diagnostic acoustic waves reflected in the body of said subject and for converting said parts into electrical signals, means for generating said image from said electrical signals, and filter means for suppressing a fundamental of the focused therapeutic acoustic waves having a transfer function with a rejection band wherein said first frequency lies and a passband wherein said second frequency lies.

2. A therapy apparatus as claimed in claim 1 wherein said filter means comprises an electronic filter circuit to which said electrical signals are supplied and which acts on said electrical signals.

3. A therapy apparatus as claimed in claim 1 wherein said means for generating therapeutic acoustic waves comprises means for generating therapeutic ultrasound and wherein said means for emitting said diagnostic acoustic waves comprises means for emitting diagnostic ultrasound.

4. A therapy apparatus as claimed in claim 1 wherein said means for generating therapeutic acoustic waves comprises means for generating therapeutic ultrasound.

5. A therapy apparatus as claimed in claim I wherein said means for emitting diagnostic acoustic waves comprises means for emitting diagnostic ultrasound.

6. A therapy apparatus as claimed in claim 1 wherein said means for emitting diagnostic acoustic waves comprises at least one ultrasound transducer which emits diagnostic ultrasound and which converts parts of said diagnostic ultrasound reflected by the body of said subject into said electrical signals.

7. A therapy apparatus as claimed in claim 6 wherein said means for generating an image from said electrical signals comprises image-generating electronics for generating ultrasound images, said image-generating electronics containing said filter means.

8. A therapy apparatus as claimed in claim 7 wherein said image-generating electronics comprises means for generating a real-time ultrasound image.

9. A therapy apparatus as claimed in claim 7 wherein said image-generating electronics comprises means for generating an ultrasound B-image.

10. A therapy apparatus as claimed in claim 1 wherein said first frequency is lower than said second frequency.

11. A therapy apparatus as claimed in claim 1 wherein said filter means comprises a high-pass filter.

12. A therapy apparatus as claimed in claim I wherein said filter means comprises a low-pass filter.

13. A therapy apparatus as claimed in claim 1 wherein said filter means comprises a band rejection filter.

14. A therapy apparatus as claimed in claim 1 wherein said filter means comprises a bandpass filter.

15. A therapy apparatus as claimed in claim 1 further comprising means, connected to said means for emitting diagnostic acoustic waves at a second frequency, for adjusting said second frequency.

16. A therapy apparatus as claimed in claim 1 wherein said means for generating therapeutic acoustic waves comprises a plurality of ultrasound transducers and means for operating said ultrasound transducers as a phased array.

17. A therapy apparatus as claimed in claim 16 wherein said plurality of ultrasound transducers are arranged in a linear array.

18. A therapy apparatus as claimed in claim 17 wherein said linear array has a longitudinal axis, and wherein said linear array is curved around an axis proceeding parallel to said longitudinal axis.

19. A therapy apparatus as claimed in claim 1 wherein said means for emitting diagnostic acoustic waves comprises a plurality of ultrasound transducers and means for operating said ultrasound transducers as a phased array.

20. A therapy apparatus as claimed in claim 19 wherein said plurality of ultrasound transducers are arranged in a linear array.

21. A therapy apparatus as claimed in claim 20 wherein said linear array has a longitudinal axis, and wherein said linear array is curved around an axis proceeding parallel to said longitudinal axis.

22. A therapy apparatus as claimed in claim 1 wherein said means for emitting diagnostic acoustic waves comprises a diagnostic ultrasound transducer, and further comprising means for rotating said diagnostic ultrasound transducer around an axis relative to said means for generating therapeutic acoustic waves.

23. A method for locating and treating a zone in the body of a living subject with acoustic waves comprising the steps of:
generating therapeutic acoustic waves at a first frequency and focusing said therapeutic acoustic waves onto a zone of action; and
generating an image of a zone to be treated in said subject simultaneously with the generation of therapeutic acoustic waves, for assisting in bringing said zone of action into coincidence with said zone to be treated, by emitting diagnostic acoustic waves at a second frequency and receiving parts of said diagnostic acoustic waves reflected in the body of said subject and converting said parts into electrical signals, and generating said image from said electrical signals, and filter, and suppressing a fundamental of the focused therapeutic acoustic waves during the generation of said image.

24. A method as claimed in claim 23 wherein the step of suppressing said fundamental is further defined by filtering said electrical signals using a transfer function with a rejection band wherein said first frequency lies and a passband wherein said second frequency lies.

25. A method as claimed in claim 24 wherein the step of generating said image is further defined by generating a real-time ultrasound image.

26. A method as claimed in claim 24 wherein the step of generating said image is further defined by generating an ultrasound B-image.

27. A method as claimed in claim 24 wherein said first frequency is lower than said second frequency.

28. A method as claimed in claim 24 wherein the step of generating therapeutic acoustic waves is further defined by the steps of generating therapeutic acoustic waves using a plurality of ultrasound transducers and operating said ultrasound transducers as a phased array.

29. A method as claimed in claim 24 wherein the step of emitting diagnostic acoustic waves is further defined by the steps of emitting diagnostic acoustic waves using a plurality of ultrasound transducers and means for operating said ultrasound transducers as a phased array.

* * * * *